(12) United States Patent
Draaijer

(10) Patent No.: US 7,695,679 B2
(45) Date of Patent: Apr. 13, 2010

(54) OPTICAL SENSOR FOR MEASURING OXYGEN

(75) Inventor: Arie Draaijer, Zeist (NL)

(73) Assignee: Nederlandse Organisatie voor Toegepast - Natuurwetenschappelijk Onderzoek TNO, Delft (NL)

( * ) Notice: Subject to any disclaimer, the term of this patent is extended or adjusted under 35 U.S.C. 154(b) by 489 days.

(21) Appl. No.: 10/204,304

(22) PCT Filed: Feb. 22, 2001

(86) PCT No.: PCT/NL01/00150

§ 371 (c)(1),
(2), (4) Date: Nov. 18, 2002

(87) PCT Pub. No.: WO01/63264

PCT Pub. Date: Aug. 30, 2001

(65) Prior Publication Data

US 2003/0143118 A1    Jul. 31, 2003

(30) Foreign Application Priority Data

Feb. 22, 2000 (NL) .................... 1014464

(51) Int. Cl.
*G01N 33/48* (2006.01)
(52) U.S. Cl. .................... 422/82.05; 422/55
(58) Field of Classification Search .............. 422/55, 422/56, 82.05–82.11
See application file for complete search history.

(56) References Cited

U.S. PATENT DOCUMENTS

| 3,839,178 | A | * | 10/1974 | Macur | 204/415 |
| 4,008,047 | A | * | 2/1977 | Petersen | 422/48 |
| 4,812,221 | A | * | 3/1989 | Madou et al. | 204/412 |
| 5,206,118 | A | * | 4/1993 | Sidney et al. | 430/343 |
| 5,338,429 | A | * | 8/1994 | Jolson et al. | 204/415 |
| 5,656,241 | A |   | 8/1997 | Seifert et al. | |
| 5,756,631 | A | * | 5/1998 | Grate | 528/26 |
| 5,965,642 | A |   | 10/1999 | Gouterman et al. | |
| 2002/0156355 | A1 | * | 10/2002 | Gough | 600/345 |

FOREIGN PATENT DOCUMENTS

GB        2 132 348        7/1984

OTHER PUBLICATIONS

Lakowicz, J.R. "Principles of Fluorescence Spectroscopy" 2d ed, Kluwer Academic/Plenum Publishers (1999), pp. 536-538.*

* cited by examiner

*Primary Examiner*—Lyle A Alexander
(74) *Attorney, Agent, or Firm*—Young & Thompson

(57) ABSTRACT

A substrate has an oxygen sensitive dye embedded therein, this sensor is chemically stable to a high degree, has a high temperature resistance in the relevant temperature range, and is gas permeable to a high extent. The substrate consists of a fluoridated silicone polymer. The substrate is a fluoridated silicone polymer and the dye is an organometallic complex.

5 Claims, 2 Drawing Sheets

OPTICAL SENSOR FOR MEASURING OXYGEN

BACKGROUND OF THE INVENTION

This invention relates to an optical sensor for measuring oxygen in a medium, provided with a substrate in which an organometallic complex is embedded.

The organometallic complex is an oxygen-sensitive fluorescent dye, with the amount of fluorescence and the fluorescence life being dependent on the oxygen content in the medium. Such an organometal typically consists of Tris-$Ru^{2+}$-4,7-biphenyl-1,10-phenanthroline; this Ru(ruthenium) complex is particularly oxygen-sensitive, but other organometals can also be used, such as an Os complex or a Pt complex.

The organometallic complex is normally adsorbed to a silica gel. The silica gel can adsorb a high concentration of the dye without the fluorescent properties of the material being thereby affected. The silica gel with the adsorbed dye is embedded in a substrate of polymeric material, for instance a mixture of PDMS (polydimethyl-siloxane) and PTMSP (polytrimethylsilylpropyl), which polymers are gas permeable to a high degree, so that the response of the sensor to oxygen content changes can be prompt. By being embedded in the substrate, the organometallic complex is rendered insensitive to disturbing influences, such as, for instance, the action of moisture or leaching of the fluorescent component.

Through fluorescence measurements, the level of the oxygen content in the medium can be determined. Such a measurement is relatively simple to carry out, but has as a disadvantage that the measuring results, owing to the occurrence of, for instance, photobleaching or ageing of the sensor due to high temperatures, are no longer reproducible with the passage of time.

This phenomenon occurs in particular if measurements are performed where the medium consists of consumable oil, such as fish oil, sunflower oil, etc. In practice, there is an interest in determining the oxygen content in such media for the purpose of assessing the storage life thereof. Through chemical action of the medium, however, measurements with the sensor applied heretofore have been found to become unreliable with the passage of time.

This phenomenon also occurs as a result of a high temperature loading of the sensor, for instance when using the sensor as a feedback for the gas-air ratio in combustion apparatus. Further, this phenomenon occurs if the sensor is exposed for a relatively long time, for instance in the case of oxygen content measurements in groundwater.

It is attempted to obviate these problems by stabilizing the sensor. This has shown that an inherently chemically stable and gas permeable substrate material is not straightforwardly satisfactory: for that, the chemical interaction with the embedded dye, which must retain its oxygen-sensitive properties, and the substrate is too complex. To date, therefore, there is not any substrate known which, in combination with the oxygen-sensitive dye, continues to retain its favorable properties.

SUMMARY OF THE INVENTION

Accordingly, the object of the invention is to solve the above-described problem and to provide a substrate for embedding oxygen-sensitive dye, while the thus formed sensor is chemically stable to a high degree, has a high temperature resistance in the relevant temperature range, and is gas permeable to a high extent.

This object is achieved in that the substrate consists of a fluoridated silicone polymer. Surprisingly, it was found from experiments that such a polymer possesses the required properties mentioned.

The invention can be applied with particular advantage if the medium is a consumable oil, such as, for instance, sunflower oil, if measurement is performed at high temperatures, or if the sensor is exposed for a relatively long time. An additional advantageous property is that the substrate has been found to adhere well to glass. As a consequence, in practice, the oxygen content can be simply determined in consumable oil products which are stored in glass, from which in turn a storage life can be derived, and the sensor will not come loose at high temperatures or in chemically aggressive environments.

In a preferred embodiment, the fluoridated silicone polymer is a polyfluoroalkyl methyl siloxane polymer which is marketed by the firm of Wacker under the trademark name of ELASTOSIL E113F. Of the tested substrate materials, this polymer has been found to exhibit the best stability at high temperature loads.

BRIEF DESCRIPTION OF THE DRAWINGS

The invention will now be further elucidated with reference to the accompanying drawing, wherein.

DETAILED DESCRIPTION OF THE PREFERRED EMBODIMENTS

Figure 1A:
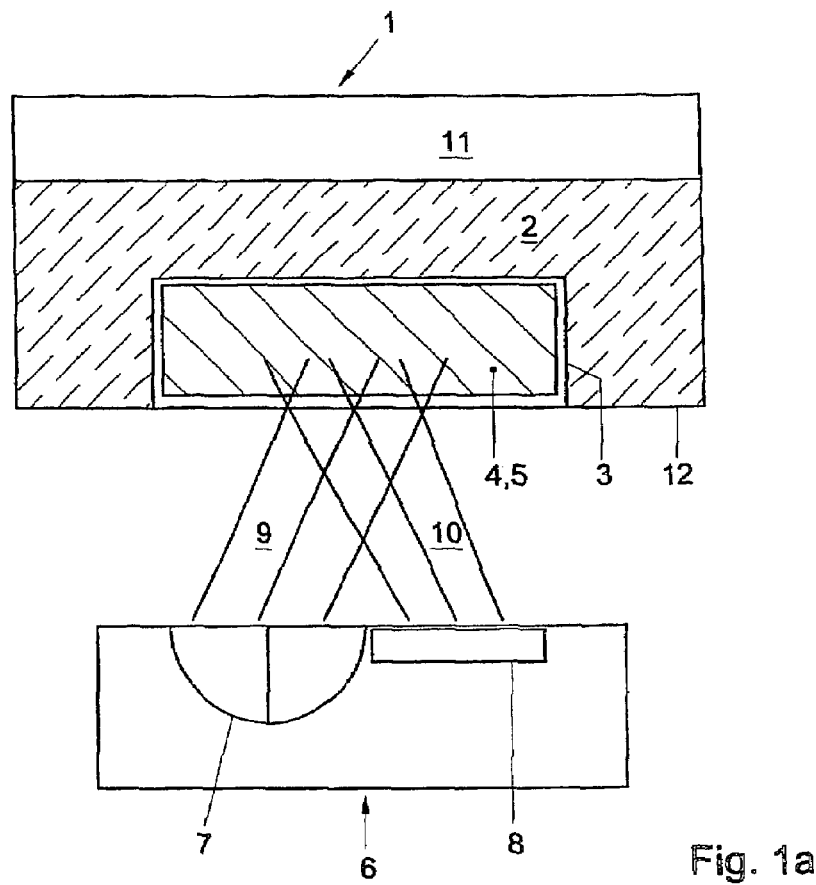
FIG. 1a shows a diagram schematically indicating how the sensor can be arranged in contact with the medium, with respect to a measuring unit, with the sensor arranged in the medium.

Referring to FIG. 1a, a light transmitting container 1, for instance of glass, contains a medium 2, for instance a consumable oil. With the arrangement, the oxygen content in oil 2 can be measured. This oxygen dissolves in the oil in that an equilibrium arises between the oxygen in the air 11 and the oxygen in the oil 2. The optical sensor 3 of the invention is arranged in the container 1 by affixing it to a wall 12. The sensor comprises a substrate 4 and an oxygen-sensitive dye 5, consisting of an organometallic complex. Light 9 of a particular wavelength spectrum, coming from a lamp 7 of a detector 6, shines on the sensor 3, thereby giving rise to fluorescence in the dye 5. The fluorescence comprises light of a different wavelength spectrum 10, which is radiated to the detector and is received on a photoelectric converter 8. According to the invention, the substrate 4 consists of a fluoridated silicone polymer. Because of the gas permeability of the substrate 4, oxygen from the oil 2 can interact with the organometallic complex. As a result, the amount of fluorescence is influenced by the amount of oxygen in the medium. By measuring the emitted intensity or life of the fluorescence 10, the extent of the influence, and hence the oxygen content, can be established.

Figure 1B:
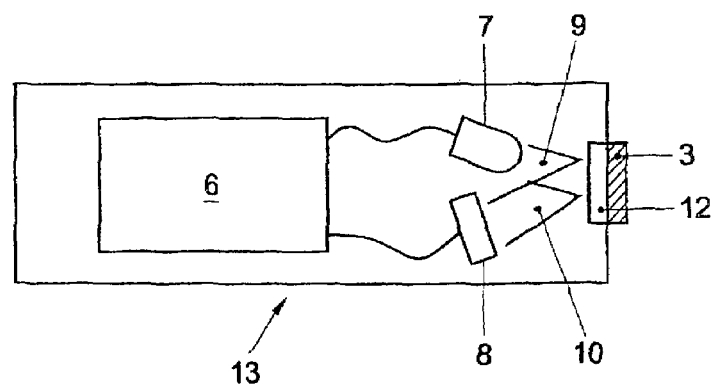
FIG. 1b shows a diagram of a combined sensor/measuring unit.

Referring to FIG. 1b, a combined sensor/measuring unit 13 contains a lamp 7 and a photoelectric converter 8 and a sensor 3 which is arranged on the outside of the sensor/measuring unit 13. With the arrangement, for instance the gas-air ratio in combustion apparatus can be measured.

Figure 2:
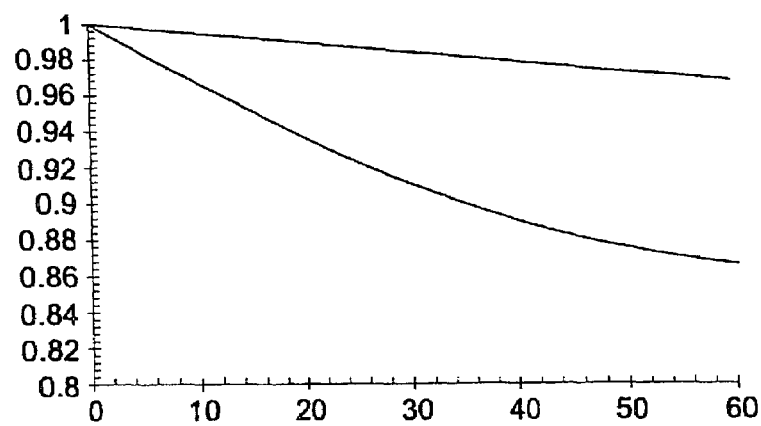
FIG. 2 shows a graph representing the resistance to photobleaching for a conventional substrate and for a substrate according to the invention.

FIG. 2 shows a graph reflecting how a sensor as indicated in FIG. 1 by reference numeral 3, in two designs, was irradiated for an hour with a constant amount of light of a high light intensity. Through the effect of photobleaching, after a few minutes, a reduced fluorescence arises, as a result of which the sensor becomes less and less sensitive. In the graph, the y-axis plots a light intensity radiated by the sensor, as a consequence of the irradiation of the sensor with a constant amount of light, normalized at 1. The x-axis plots the time, in minutes, when fluorescence was measured. It can be derived from the graph that the effect of photobleaching is considerably less for a sensor with a substrate consisting of fluoridated silicone polymer (upper line) than for a sensor with a substrate of a conventional silicone polymer (lower line). It is incidentally noted that under normal operating conditions, the light intensity used is much lower, so that the phenomena do not occur so soon. However, the deviation remains proportionally the same.

Figure 3:
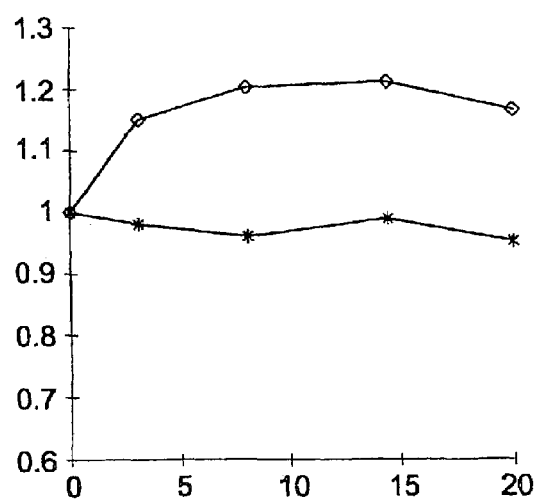
FIG. 3 shows a graph representing the resistance to chemical action of sunflower oil for a conventional substrate and for a substrate according to the invention.

FIG. 3 represents a graph reflecting the resistance to chemical action of sunflower oil for a conventional substrate and for a substrate according to the invention; in both tests a sensor was placed in sunflower oil over a prolonged period of time of a few weeks, while the sunflower oil was exposed to air. At regular intervals the time of decay of the fluorescence was measured, i.e., the time when the intensity has decreased to 1/e. Through action of the oil, for a conventional substrate, this decay time increases after some time, i.e. the sensitive substance remains fluorescent longer than in the case where no action of oil takes place, despite the fact that the oxygen concentration remains constant. The sensitivity of the sensor is therefore influenced by the action, so that no reliable measurement of the oxygen content can be made. In the graph, the y-axis plots this time of decay, normalized at 1, against the time of measurement, in days, plotted on the x-axis. It can be derived from the graph that a sensor with a substrate consisting of fluoridated silicone polymer (lower line) has a much better, substantially constant, resistance to chemical actions than does a sensor with a substrate of a conventional silicone polymer (upper line).

Figure 4:
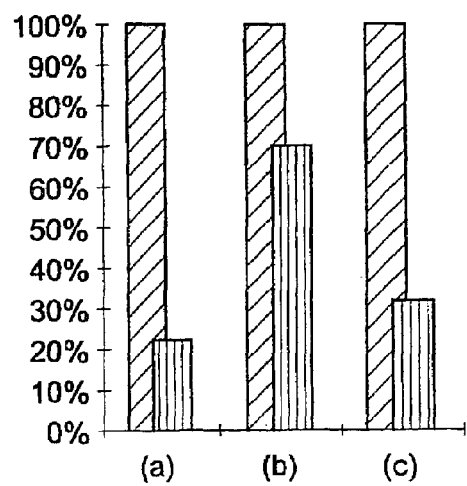
FIG. 4 shows a chart representing the resistance to temperature loading for a conventional substrate and for a substrate according to the invention.

FIG. 4 is a chart representing the resistance to temperature loads for a conventional substrate and for a substrate according to the invention; in both tests, a sensor was exposed to air at a high ambient temperature for five weeks. In the chart it can be seen that after exposure to this temperature a reduced fluorescence occurs, so that the sensor becomes less sensitive. In the chart, the y-axis plots a light intensity radiated by the sensor, as a result of the irradiation of the sensor with a constant amount of light, normalized at 100%. For each of three different substrate materials, the x-axis plots two respective measurements, one in which the sensor was stored at 20° C. and one in which the sensor was stored at 90° C. From the chart, it can be derived that for a conventional silicone polymer (a) the intensity of the sensor decreases to 20% of the value with respect to the sensor stored at room temperature. The sensitivity of the sensor therefore decreases considerably. For a sensor with a substrate according to the invention (a mixture of PS184.5 and PS9120 of the firm United Chemicals Inc), the sensitivity decreases comparatively less, to about 30%, so that, compared with the conventional sensor, an improved temperature resistance is achieved (c). For a sensor according to the preferred embodiment, i.e., a sensor with a substrate of the polyfluoroalkyl methyl siloxane type such as ELASTOSIL E113F of the firm of Wacker, this temperature influence is a factor 2 less high and the intensity remains up to 70% of the value at room temperature (b).

The invention is not limited in any way to the exemplary embodiments described and represented here, but encompasses all kinds of modifications, naturally insofar as they fall within the scope of protection of the claims following below.

The invention claimed is:

1. An optical sensor for measuring oxygen in a medium, said optical sensor comprising:
   a substrate consisting essentially of a fluoridated polyfluoralkyl methyl siloxane polymer; and
   an organometallic complex embedded in said substrate, said organometallic complex fluorescing when subject to light, said substrate stabilizing the organometallic complex against photobleaching and thermal degradation,
   wherein the organometallic complex is selected from the group consisting of Ru, Os and Pt complexes.

2. The optical sensor according to claim 1, wherein the organometallic complex is an Ru complex.

3. The optical sensor according to claim 1, wherein the organometallic complex is an Os complex.

4. The optical sensor according to claim 1, wherein the organometallic complex is a Pt complex.

5. The optical sensor according to claim 1, wherein organometallic complex is adsorbed to a silica gel, and the silica gel and the organometallic complex are embedded in said substrate.

* * * * *